United States Patent [19]

Tamm

[11] 4,094,607

[45] June 13, 1978

[54] APPARATUS FOR FLAMELESS ATOMIZATION OF A SAMPLE FOR ATOMIC ABSORPTION ANALYSIS

[75] Inventor: Rolf Gunther Arnold Tamm, Salem, Germany

[73] Assignee: Bodenseewerk Perkin-Elmer & Co., GmbH, Uberlingen, Germany

[21] Appl. No.: 779,559

[22] Filed: Mar. 21, 1977

[30] Foreign Application Priority Data

Mar. 27, 1976 Germany .............................. 2613196

[51] Int. Cl.² .......................... G01J 3/30; G01N 21/16
[52] U.S. Cl. ........................................ 356/85; 356/244
[58] Field of Search ................................... 356/85, 244

[56] References Cited

U.S. PATENT DOCUMENTS 3,702,219  11/1972  Braun et al. ...................... 356/85 X
3,979,162  9/1976  George ................................ 356/85
4,022,530  5/1977  Braun et al. ...................... 356/85

Primary Examiner—F. L. Evans
Attorney, Agent, or Firm—Sal A. Giarrantana; Francis L. Masselle; Edwin T. Grimes

[57] ABSTRACT

The present invention is directed to apparatus for flameless atomization of a sample for atomic absorption analysis, which includes a sample tube of electrically conductive material having a transverse bore offset axially towards one end of the tube with respect to the transverse central plane, an electrode arrangement including portions in electrical contact with the sample tube at spaced locations for passing an electrical current through the tube to cause heating thereof, and a system for generating an inert gas flow inwardly from the opposite end of the sample tube and outwardly through the transverse bore.

6 Claims, 1 Drawing Figure

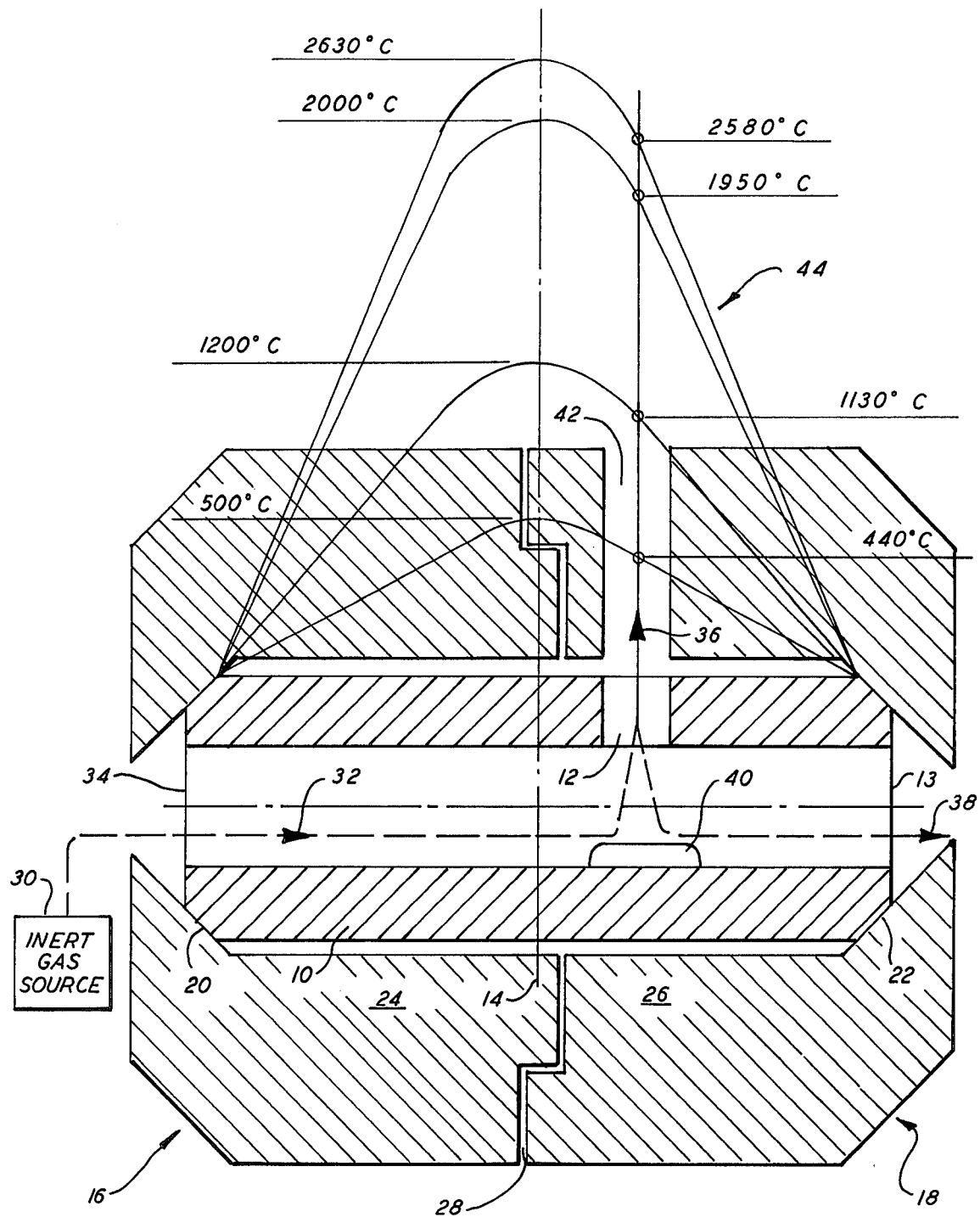

APPARATUS FOR FLAMELESS ATOMIZATION OF A SAMPLE FOR ATOMIC ABSORPTION ANALYSIS

BACKGROUND OF THE INVENTION

The invention relates to a graphite tube and related elements for an atomizing device, which are used in flameless atomic absorption spectroscopy.

An atomizing device is known from German patent specification 2 314 207 in which the graphite tube is heated by passing an electrical current therethrough. An inert gas flow is directed inwardly from the ends of the tube, through the tube, and discharged through a transverse bore. In this prior art atomizing device, the transverse bore is located in the transverse central plane, which is exactly halfway between the ends of the graphite tube. It will be appreciated that this center is also the hottest portion of the graphite tube, as the ends thereof are in heat exchange relationship with the electrodes or contact pieces, to which the current to the graphite tube is conducted, and the electrodes are mounted in cooling jackets. As a consequence, the inert gas flow is directed from the cooler surface areas of the graphite tube to the hotter ones to prevent substances carried by the flow from being deposited on the cooler surface areas.

Furthermore, it is known from U.S. patent application Ser. No. 608,558, dated Aug. 28, 1975, now U.S. Pat. No. 4,022,530, to make the electrodes tubular, so that they together surround the graphite tube like a jacket. According to this patent specification, one of the electrodes is longer than the other one, so that the parting line therebetween is unsymmetrical with respect to the center of the graphite tube. The electrode, which is longer, has a transverse bore aligned with the transverse bore of the graphite tube.

In practice, the prior art arrangements present some problems. By providing the transverse bore for the feeding of the sample in the center of the graphite tube, there is a mechanical weakening of the graphite tube in its hottest zone, thereby reducing the useful life of the graphite tube. In addition, the gas flow tends to remove graphite particles from the transverse bore in this hottest zone. This is particularly true when, after the drying, decomposing and atomizing of the sample, the tube is heated to its maximum temperature, with maximum inert gas flow, in order to prepare it for the next measurement.

As another technical problem, it is difficult to achieve equal gas flow from both ends of the tube, and hence, accurately adjusted flow producing means must be provided. Further, the placing of a liquid sample at the maximum of the temperature profile can result in splitting-up of the sample and sputtering during vaporization, because the sample is heated to its greatest extent at its center and starts vaporizing from that point.

In the arrangement of U.S. patent application Ser. No. 608,558, now U.S. Pat. No. 4,022,530, the heat dissipating from the two jacket-shaped electrodes to the cooling jackets differ, because they receive different proportions of the radiation from the graphite tube, due to their differences in length. In addition, the requirement of having electrodes of different lengths increases the manufacturing and storage costs.

SUMMARY OF THE INVENTION

An object of the present invention resides in the provision of a graphite tube for an atomizing device, which is used in flameless atomic absorption spectroscopy, that has an increased useful life as compared to prior art such graphite tubes.

Another object of the invention is the provision of a graphite tube with which the flow conditions of the inert gas are more stable than with prior art graphite tubes, and with which the electrodes are of substantially symmetrical design.

To the accomplishment of the foregoing objectives and additional objectives and advantages, which will become apparent as the description proceeds, the invention contemplates the provision of a new and improved apparatus for flameless atomization of a sample for atomic absorption analysis which includes, in combination, a sample tube of electrically conductive material such as, for example, graphite, which has a transverse bore offset axially towards one end of the tube with respect to the transverse central plane. The combination includes electrode means having portions in electrical contact with the sample tube at spaced locations for passing an electrical current through the tube to cause heating thereof. Means are provided for generating an inert gas flow inwardly from the opposite end of the sample tube and outwardly through the transverse bore.

According to one aspect of the invention, the electrode means comprise two substantially symmetrical electrodes. According to another aspect thereof, the electrodes have portions which are spaced from the sample tube and which substantially envelope and shield the tube against radiation. According to still another aspect of the invention, these electrode portions have complementary, radially-stepped configurations defining a radially-stepped parting line space therebetween.

There has thus been outlined rather broadly the more important features of the invention in order that the detailed description thereof that follows may be better understood, and in order that the present contribution to the art may be better appreciated. There are, of course, additional features of the invention which will be described fully hereinafter. Those skilled in the art will appreciate that the conception on which this disclosure is based may readily be utilized as the basis of the designing of other structures for carrying out the purposes of the invention. It is important, therefore, that this disclosure be regarded as including such equivalent constructions as to do not depart from the spirit and scope of the invention.

One embodiment of the invention has been chosen for purposes of illustration and description, and is shown in the accompanying drawing forming a part of the specification.

BRIEF DESCRIPTION OF THE DRAWING

The FIGURE of the drawing is a longitudinal sectional view of apparatus for flameless atomization of a sample for atomic absorption analysis constructed in accordance with the concepts of the invention, with temperature profiles being shown which correspond to different values of the heating current.

DETAILED DESCRIPTION OF THE PREFERRED EMBODIMENT

In the embodiment of the invention illustrated, the apparatus for flameless atomic atomization of a sample for atomic absorption analysis includes a cylindrical sample tube 10 of electrically conductive material, such as graphite, for example. The sample tube has a transverse bore 12, which is offset axially with respect to the transverse central plane 14, towards the right-hand end 13 of the graphite tube, as viewed in the FIGURE. Two substantially symmetrical electrodes, indicated at 16 and 18, have portions which are in electrical contact with the sample tube at spaced locations 20 and 22, respectively, for passing an electrical current through the tube to cause heating thereof. In the form of the invention illustrated, the electrodes 16 and 18 include portions 24 and 26, respectively, which are spaced from the sample tube and which substantially envelope and shield the tube against radiation. The electrode portions 24 and 26 have complementary, radially-stepped configurations which define a radially-stepped parting line space 28 between them.

In addition, the apparatus includes an inert gas source, indicated schematically at 30 in the drawing, which generates an inert gas flow inwardly, as indicated by arrow 32, from the end 34 of the sample tube 10 and outwardly through the transverse bore 12, as indicated by arrow 36. Also, a portion of the inert gas flows outwardly through the end 13 of the tube, as indicated by arrow 38.

The graphite tube 10 is adapted to receive a sample 40 through the transverse bore 12 in the tube and a mating bore 42 in the electrode 18. In operation, the tube is heated to effect, sequentially, drying, ashing and atomization of the sample, and a beam of radiation, of selected spectral characteristics, is directed through the tube to effect analysis of the atomized sample in a manner well known in the art of atomic absorption spectroscopy. In this connection, reference may be had to U.S. Pat. No. 2,847,899.

Referring to the figure, temperature profiles indicated generally at 44, are shown which correspond to different values of the heating current. The maxima of the temperature profiles are located in the transverse central plane 14 so that the transverse bore 12 is always at a lower temperature than the maximum temperature for any given profile. Thus, for example, for the maximum heating of the graphite tube, the maximum temperature in the transverse central plane 14 is 2,630° C whereas the temperature in the area of the transverse bore 12 is 2,580° C. This ensures that the maximum temperature and the weak point of the graphite tube, due to the transverse bore, do not coincide. It has been found that the total useful life of the graphite tube can be increased thereby.

In addition, due to the unsymmetrical arrangement of the transverse bore 12, an unsymmetrical inert gas flow can be used, whereby a stable inert gas flow condition can be achieved more easily than with the conventional symmetrical arrangement of the transverse bore, which required two substantially equal flows in order to avoid reversal of the flow towards one or the other end of the tube. According to the invention, the inert gas flow, as viewed by the sample, is always in the same direction, during all of the analytical steps. Moreover, the electrodes are substantially symmetrically disposed.

It is true that in the graphite tube of the invention, a portion of the inert gas flows from the hotter to the cooler surface areas, adjacent the end 13 of the tube. However, this adverse effect (deposition) resulting therefrom may be eliminated by heating the graphite tube after each analysis.

Having thus described the invention with particular reference to the preferred form thereof, it will be obvious to those skilled in the art to which the invention pertains, after understanding the invention, that various changes and modifications may be made therein without departing from the spirit and scope of the invention, as defined by the claims appended hereto.

What is claimed is:

1. Apparatus for flamesless atomization of a sample for atomic absorption analysis comprising:

a sample tube of electrically conductive material, said sample tube having a transverse bore offset axially towards one end of the tube with respect to the transverse central plane;

electrode means including portions in electrical contact with said sample tube at spaced locations for passing an electrical current through the tube to cause heating thereof; and means for generating an inert gas flow inwardly from the end opposite said one end of the sample tube and outwardly through said transverse bore.

2. Apparatus according to claim 1 wherein said sample tube is of cylindrical configuration and is fabricated from graphite.

3. Apparatus according to claim 1 wherein a portion of said inert gas flows outwardly through said one end of the sample tube.

4. Apparatus according to claim 1 wherein said electrode means includes two substantially symmetrical electrodes.

5. Apparatus according to claim 4 wherein said electrodes include portions spaced from and substantially enveloping and shielding said sample tube against radiation.

6. Apparatus according to claim 5 wherein said electrode portions have complementary, radially-stepped configurations defining a radially-stepped parting line space between them.

* * * * *